(12) United States Patent
Sablatschan et al.

(10) Patent No.: US 10,376,348 B2
(45) Date of Patent: Aug. 13, 2019

(54) SHAFT FOR AN AUTOMATIC TOOTHBRUSH

(71) Applicant: KONINKLIJKE PHILIPS N.V., Eindhoven (NL)

(72) Inventors: Siegfried Sablatschan, Ferlach (AT); Rene Michael Brunner, Klagenfurt (AT); Christian Martin Rassi, St. Andra (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 183 days.

(21) Appl. No.: 15/319,069

(22) PCT Filed: Jun. 30, 2015

(86) PCT No.: PCT/IB2015/054898
§ 371 (c)(1),
(2) Date: Dec. 15, 2016

(87) PCT Pub. No.: WO2016/001831
PCT Pub. Date: Jan. 7, 2016

(65) Prior Publication Data
US 2017/0119511 A1    May 4, 2017

Related U.S. Application Data

(60) Provisional application No. 62/020,072, filed on Jul. 2, 2014.

(51) Int. Cl.
*A61C 17/22* (2006.01)
*F16C 3/18* (2006.01)

(52) U.S. Cl.
CPC .......... *A61C 17/222* (2013.01); *A61C 17/225* (2013.01); *F16C 3/18* (2013.01)

(58) Field of Classification Search
CPC ..... A61C 17/222; A61C 17/34; A61C 17/225; A61C 17/22; A61C 15/047; F16C 3/18
USPC ........................................................ 15/22.1
See application file for complete search history.

(56) References Cited

U.S. PATENT DOCUMENTS

| | | | |
|---|---|---|---|
| 5,815,875 A | 10/1998 | Yamada | |
| 6,851,150 B2 | 2/2005 | Chiang | |
| 8,474,085 B2 | 7/2013 | Krebner | |
| 2003/0000033 A1* | 1/2003 | Lev | A61C 17/22 15/28 |
| 2004/0045106 A1 | 3/2004 | Lam | |

(Continued)

FOREIGN PATENT DOCUMENTS

| | | |
|---|---|---|
| CN | 201064496 Y | 5/2008 |
| EP | 2263496 A1 | 12/2010 |
| EP | 2538817 B1 | 12/2013 |

(Continued)

*Primary Examiner* — Laura C Guidotti (57) ABSTRACT

An automatic toothbrush (100), including: a body (102) having opposed ends, a cavity (105) situated between the opposed ends, and an opening (107) situated at one of the opposed ends; an output shaft (120) having first and second ends (124, 122) and extending through the opening such that the second end (122) is outside of the cavity, the output shaft having a plurality of bends (139, 141, 143,145) situated between the second end and the opening; and an oral cleaning tool (104) configured to be press fit onto that portion of the shaft which has the plurality of bends.

10 Claims, 8 Drawing Sheets

(56) References Cited

U.S. PATENT DOCUMENTS

2005/0102774 A1   5/2005   Drossler

FOREIGN PATENT DOCUMENTS

| WO | 2004028293 A1 | 4/2004 | |
|---|---|---|---|
| WO | 2009000467 A1 | 12/2008 | |
| WO | 2009009860 A1 | 1/2009 | |
| WO | 2011103962 A1 | 9/2011 | |
| WO | 2013061219 A1 | 5/2013 | |
| WO | WO 2016/189444 A1 * | 12/2016 | ........... A61C 17/224 |

* cited by examiner

SHAFT FOR AN AUTOMATIC TOOTHBRUSH

CROSS-REFERENCE TO PRIOR APPLICATIONS

This application is the U.S. National Phase application under 35 U.S.C. § 371 of International Application No. PCT/IB2015/054898, filed on Jun. 30, 2015, which claims the benefit of U.S. Provisional Patent Application No. 62/020,072, filed on Jul. 2, 2014. These applications are hereby incorporated by reference herein.

This application claims the benefit or priority of and describes relationships between the following applications: wherein this application claims the priority of U.S. Provisional Patent Application Ser. No. 62/020,072, filed Jul. 2, 2014, which is incorporated herein in whole by reference.

The present system relates to an automatic (e.g., electronic) toothbrush and, more particularly, to an automatic toothbrush having a single-piece offset output shaft, and a method of manufacture thereof.

Oral healthcare is an important element in personal care. Conventional automatic toothbrushes may have rotating and/or vibrating oral cleaning tools, such as brush heads, to effectively clean teeth and remove plaque. The oral cleaning tools are attached to, and driven by, an output shaft of the automatic toothbrush, which is typically formed from multiple assembled elements, some of which are machined. For example, exterior portions of these output shafts are typically turned and machined to form a semicircular cross-sectional shape suitable for attachment to the oral cleaning tools. The multiple-element design and method of manufacture (e.g., the machining and turning) increases manufacturing complexity and cost. Further, the multiple-element design is more prone to emitting noise. Accordingly, embodiments of the present system provide an automatic toothbrush which may amongst other things overcome the disadvantages of the prior art systems.

The system(s), device(s), method(s), arrangements(s), user interface(s), computer program(s), processes, etc. (hereinafter each of which will be referred to as system, unless the context indicates otherwise), described herein may address problems in prior art systems.

In accordance with embodiments of the present system, there is disclosed an automatic toothbrush, including a body portion having opposed ends, a cavity situated between the opposed ends, and an opening situated at one of the opposed ends; an output shaft having first (proximal) and second (distal) ends, the distal end extending through the opening outside of the cavity, the output shaft having a plurality of bends situated between the first end and the second end; and an oral cleaning tool configured to be press fit onto that portion of the shaft which extends through the opening of the body. The output shaft may include at least one saddle situated between at least two adjacent bends of the plurality of bends. The plurality of bends may include two pairs of bends, each pair of bends comprising bends in opposite directions with a saddle situated there between.

The output shaft may be a unitary output shaft formed from a single sheet of material, or formed from multiple sheets of material joined together. The automatic toothbrush may include a socket configured to be press fit to the output shaft. The socket may have a square or rectangular cross-section. The automatic toothbrush is designed to receive an oral cleaning tool, such as a toothbrush brushhead, onto the distal end of the output shaft. At least one actuator may be configured to reciprocally drive the output shaft. The output shaft may further include at least two saddles separate from each other and situated adjacent to at least one of the plurality of bends.

In accordance with embodiments of the present system, there is disclosed an automatic toothbrush, including: a body defining a cavity and an opening leading to the cavity; an output shaft defining a longitudinal axis and having opposed first and second ends, the output shaft extending through the opening such that the first end is located within the cavity and the second end is located outside of the cavity, the output shaft deviating orthogonally to the longitudinal axis at folds to define at least one saddle between the opening and the second end; an oral cleaning device coupled to the output shaft and having a handle and a socket disposed at one end of the handle; and an actuator situated within the cavity and configured to reciprocally drive the output shaft. A cross-sectional shape of the output shaft may vary between the opening and the second end of the output shaft. The output shaft may further include a detent portion situated at the opening and having a plurality of rounded edges configured to receive a shaft seal for sealing the cavity.

The output shaft may be a unitary output shaft formed from a single sheet of material, or multiple sheets of material joined together. The actuator may include a motor or vibrator which outputs a reciprocating motion to drive the output shaft. Adjacent folds may be in opposite directions to each other. The saddle may be situated between two of the folds.

In accordance with embodiments of the present system, there is disclosed an automatic toothbrush including: a body portion having opposed ends, a cavity situated between the opposed ends, and an opening leading to the cavity; an output shaft having first and second ends, the output shaft extending through the opening such that the second end is outside of the cavity, the output shaft having a plurality of folds which define a plurality of saddles situated between the second end and the opening; and an oral cleaning tool configured to be press fit onto the output shaft. The plurality of folds may include at least two folds in opposite directions. The output shaft may be a unitary output shaft formed from a single piece of material having opposed first and second major surfaces.

The present invention is explained in further detail in the following exemplary embodiments and with reference to the figures, where identical or similar elements are indicated by the same or similar reference numerals, and the features of various exemplary embodiments being combinable. In the drawings.

The following are descriptions of illustrative embodiments that when taken in conjunction with the following drawings may demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1:
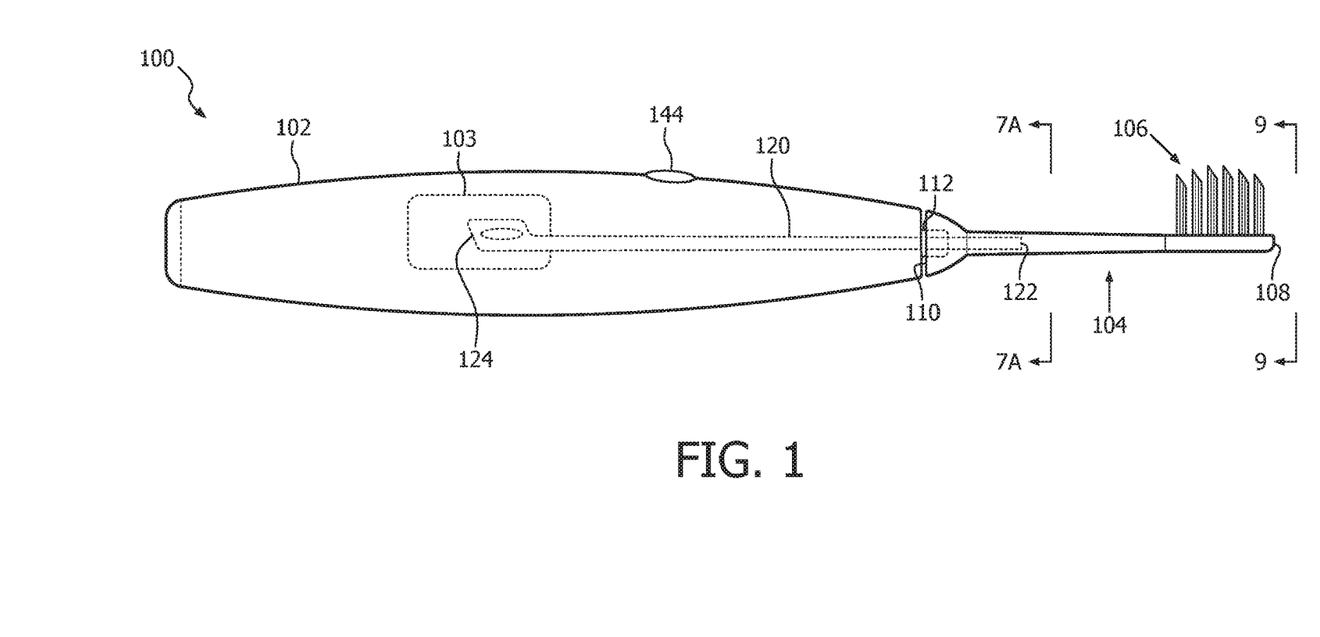
FIG. 1 shows a side planar view of a portion of an automatic toothbrush in accordance with embodiments of the present system.

FIG. 1 shows a side planar view of a portion of an automatic toothbrush 100 in accordance with embodiments of the present system. The automatic toothbrush 100 may include a body 102 having a cavity 105 therein. An oral cleaning tool 104 may be coupled to an output shaft 120 which extends from an opening 107 at one end of the body 102. A seal 112 may be provided to seal an area of the opening 107 which surrounds the output shaft 120. The seal 112 may be suitable for preventing liquids outside of the cavity from passing into the cavity 105 and may also provide for movement of the output shaft 120 during operation. The output shaft 120 may include first (proximal) and second (distal) ends 124 and 122, respectively, wherein the first end 124 is located within the cavity 105 and the second end 122 is located outside of the cavity 105. The oral cleaning tool 104 may include proximal and distal ends 110 and 108, respectively, and bristles 106 situated at the distal end 108. The oral cleaning tool 104 includes a socket which may be removably coupled to the second (distal) output shaft end 122.

An actuator 103 for driving the output shaft 120 may be situated within the cavity 105 and coupled to the output shaft 120. The actuator 103 may include any suitable electromotive device (e.g., a linear and/or rotary motor, an ultrasonic oscillating motor, etc.) which may provide a reciprocating electro-motive force to drive the output shaft 120 in one or more directions as may be desired. The output shaft 120 may be coupled to the body 102 and/or the actuator 103 such that it may move with one or more degrees of freedom as may be desired. The oral cleaning tool 104, such as a brush head, may be coupled to the body 102 via the output shaft 120 and receive a motive force (e.g., rotary force, vibrational force) from the actuator 103 which is suitable for oral care. In some embodiments, the actuator 103 may include a transmission to change rotational speed and/or direction of an output of the actuator 103. A user interface (UI) such as an on/off switch 101 may be provided so that a user may interface with the automatic toothbrush 100 and may turn the actuator 103 on or off. The UI may also be used to select an operating mode as may be desired. A controller (e.g., a processor) may control the overall operation of the automatic toothbrush 100. For example, the controller may control an operating mode of the actuator 103. Further, the controller may obtain operating parameters from a memory of the automatic toothbrush 100, in accordance with embodiments of the present system.

Figure 2:
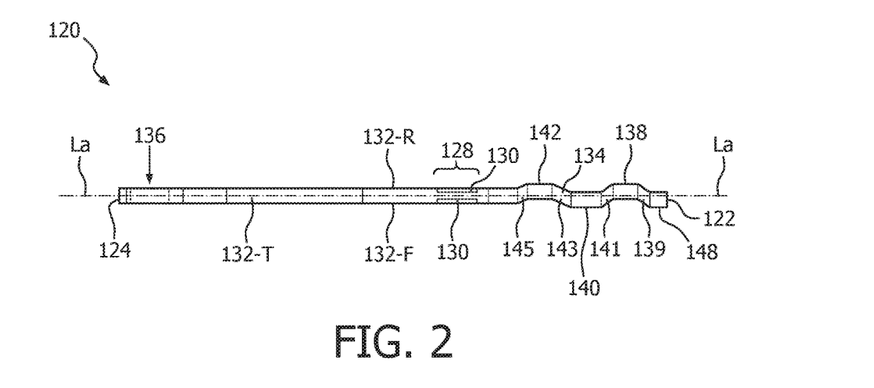
FIG. 2 shows a top planar view of a portion of the output shaft of an automatic toothbrush in accordance with embodiments of the present system.
Figure 3:
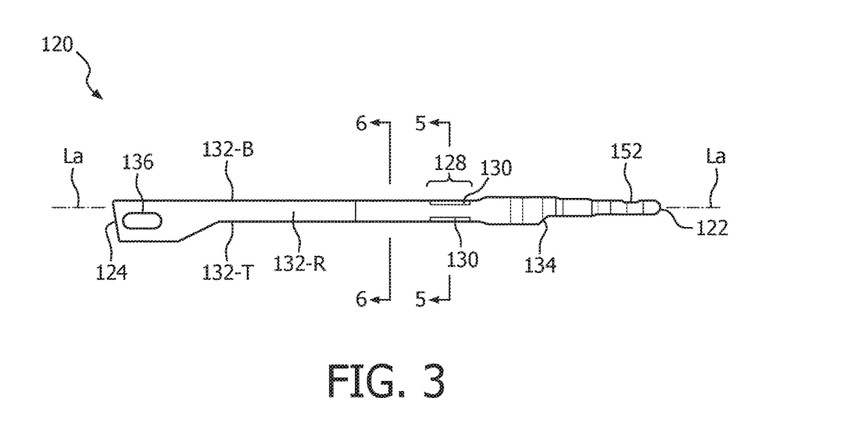
FIG. 3 shows a side planar view of a portion of the output shaft of an automatic toothbrush in accordance with embodiments of the present system.

FIGS. 2 and 3 show top and side planar views of a portion of an output shaft 120 of an automatic toothbrush 100 in accordance with embodiments of the present system. The output shaft 120 which may be a stamped piece of metal, or multiple layers of metal or other material joined together, having a plurality of sides which may form multiple surfaces. Illustratively, these surfaces may be known as a top surface 132-T, a bottom surface 132-B, a front surface 132-F and a rear surface 132-R. The top surface 132-T and the bottom surface 132-B are opposed to each other. The front surface 132-F and the rear surface 132-R are opposed to each other and may be adjacent to the front surface 132-F and rear surface 132-R. The output shaft 120 extends along a longitudinal axis (La) and may include at least one area which deviates from the longitudinal axis. For example, platform areas, or saddles 148, 138, 140 and 142 may be positioned at different distances and angles from the longitudinal axis of the output shaft 120 and be configured to contact an adjacent portion of a socket of the oral cleaning tool 104 as is described herein. The saddle areas may alternatively deviate in position from one saddle area to an adjacent saddle area towards or away from the longitudinal axis (La). For example, a first saddle area may be relatively further from the longitudinal axis than a second adjacent saddle area. Further a third saddle area that is adjacent to the second saddle area but that is not adjacent to the first saddle area may be relatively further from the longitudinal axis than the second saddle area.

Further, the saddle areas 148, 138, 140 and/or 142 may be separated from adjacent saddle areas and/or from a center portion of the output shaft 120 by folds 145, 143, 141, and 139 (e.g., deviations, bends, etc. which extend between the front and rear surfaces 132-F and 132-R, respectively). In accordance with embodiments of the present system, the saddle areas 148, 138, 140, and 142 may be created during a stamping process such as a coining process. Coining is a fleshless, precision cold forging operation in which a mechanical press is used to apply large amounts of force to the work piece when it is in the die to achieve fine detail in the part. A sealing area 128 (e.g., a detent region) may include corners with rounded edges 130. The sealing area 128 may be formed during the coining process. An opening 136 may extend through the output shaft 120 (e.g., from the front surface 132-F to the rear surface 132-R) and may be suitable to secure the shaft. A bottom planar view of the output shaft 120 may be similar to the present drawing although embodiments of the present system may also vary therefrom although not shown, for the sake of clarity. The output shaft 120 may include a base platform 134 and a detent 152 which may frictionably engage a latch of a socket of an oral cleaning 104.

Figure 4:
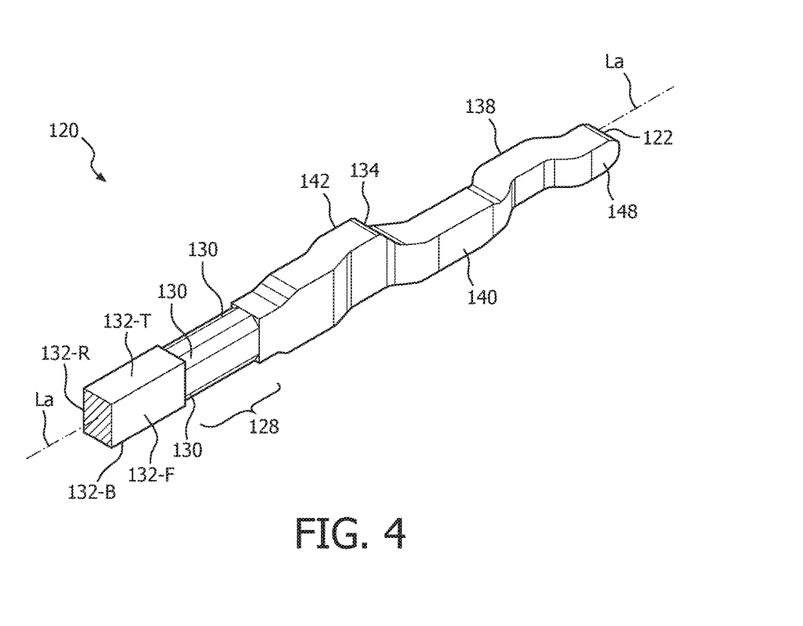
FIG. 4 shows a front isometric side view of a portion of the output shaft of an automatic toothbrush in accordance with embodiments of the present system.

FIG. 4 shows a front isometric side view of a portion of an output shaft 120 of an automatic toothbrush 100 in accordance with embodiments of the present system. As shown, a base platform 134 may extend to at least one of the saddles 138, 140 142, and 148. The sealing area 128 and rounded edges 130 of the sealing area 128 can be seen more clearly.

Figure 5:
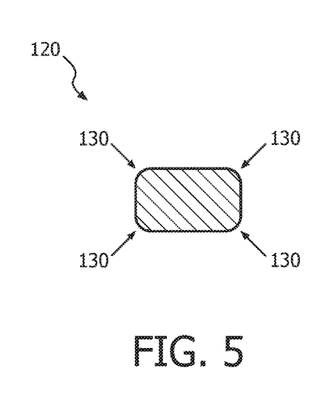
FIG. 5 shows a cross-sectional view of a portion of the output shaft taken along lines 5-5 of FIG. 3 in accordance with embodiments of the present system.

FIG. 5 shows a cross-sectional view of a portion of an output shaft 120 such as may be for example taken along lines 5-5 of FIG. 3 in accordance with embodiments of the present system. Each of the corners of the sealing area 128 may include rounded edges 130 which in accordance with embodiments of the present system may be formed during a coining process.

Figure 6:
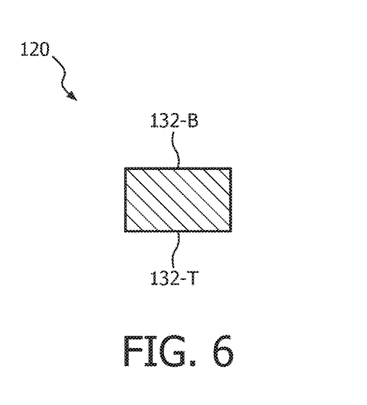
FIG. 6 shows a cross-sectional view of a portion of an output shaft such as may be for example taken along lines 6-6 of FIG. 3 in accordance with embodiments of the present system.

FIG. 6 shows a cross-sectional view of a portion of an output shaft 120 such as may be for example taken along lines 6-6 of FIG. 3 in accordance with embodiments of the present system. In accordance with embodiments of the present system, the output shaft may have a generally square or rectangular cross section, although corners may be rounded as desired.

Figure 7A:
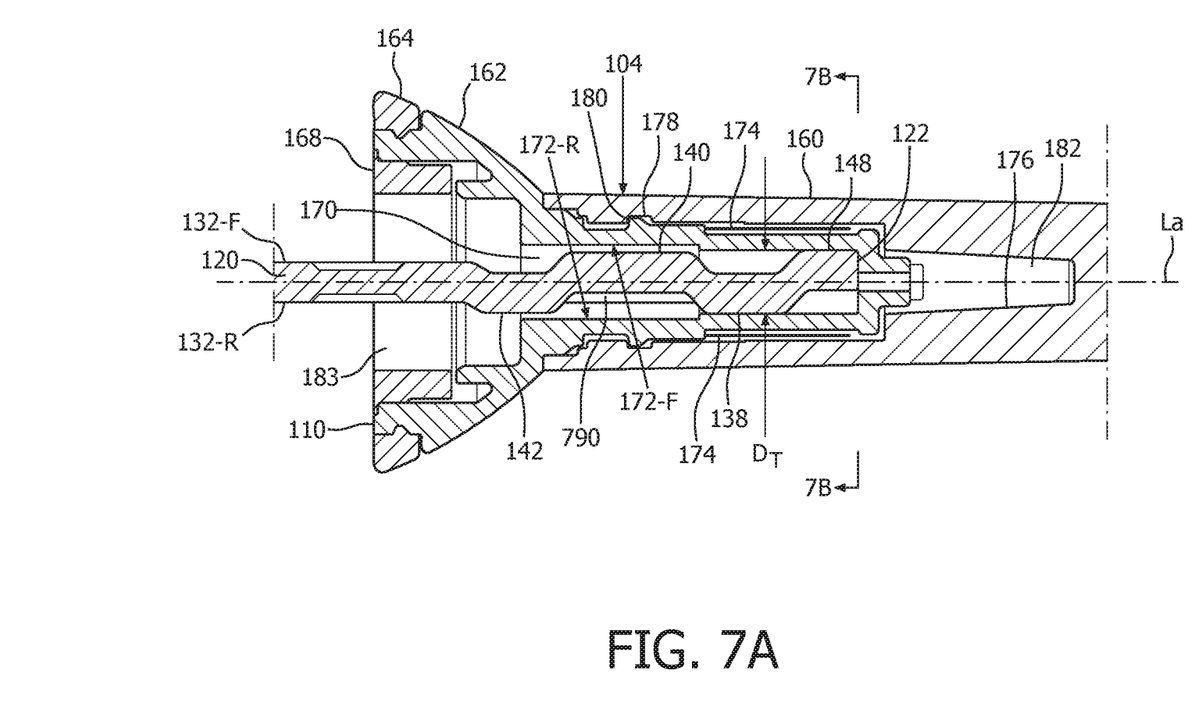
FIG. 7A shows a rear planar side view of a portion of an output shaft and a tool of an automatic toothbrush in accordance with embodiments of the present system.

FIG. 7A shows a cross sectional view of a portion of an output shaft 120 and an oral cleaning tool 104 of an automatic toothbrush 100 for example taken along lines 7A-7A of FIG. 1 in accordance with embodiments of the present system. The oral cleaning tool 104 may include a handle 160, a base 162, a ring 164, and a harmonic mass 168. The handle 160 may have a cavity 182 defined by an interior wall 176 of the handle 160. The base 162 may be at least partially inserted within the cavity 182 and may be fixedly coupled to the interior wall 176 of the oral cleaning tool cavity 182 using any suitable attachment method such as a friction fit (illustratively shown using tabs 180 illustratively of the base 162 and notches 178 in the handle 160. However, in yet other embodiments, it is envisioned that other attachment methods may be suitably applied such as adhesives, welds, etc. The ring 164 may be removably coupled to the base 162 using any suitable method(s) such as a friction fit and may in accordance with embodiments of the present system be operative to provide color coding, for example for identification. The harmonic mass 168 may be situated in a cavity 183 of the base 162 and may have a suitable mass for tuning a resonance frequency of a drive system of the automatic toothbrush 100 in accordance with embodiments of the present system. The harmonic mass 168 may have a suitable shape such as a ring and may be fixedly coupled to the base 162 using any suitable method such as adhesives, bonds, friction fits, etc.

The tool oral cleaning 104 may be releasably coupled to the output shaft 120 using any suitable method such as a friction fit (e.g., a press fit), or the like. For example, the oral cleaning tool 104 may include a socket 170 into which at least a portion of the output shaft 120 may be inserted and releasably held in position using, for example, a friction fit. The socket 170 may include a plurality of interior walls such as a front wall 172-F and an opposed a rear wall 172-R, as well as a top wall 172-T and an opposed bottom wall, 172-B, (see FIG. 7B). These interior walls will generally be referred to as walls 172-x. Accordingly, at least two of the walls 172-x of the socket 170 may engage adjacent surfaces of the output shaft 120 such as at the saddles 138, 140, 142, 148. For example, in accordance with some embodiments, the base 162 may form at least a portion of the socket 170 which engages the output shaft 120 such as at the saddles 148, 138, 140 and 142. By deviating the saddles 148, 138, 140, and 142 away from the longitudinal axis (La) of the output shaft 120, a larger saddle cross-sectional footprint may be obtained for engaging the interior portion of the socket 170 such as at the walls 172-x. A biasing member 174 (e.g. steel c-clip spring) may be provided to bias the base 162 against the interior wall of the oral cleaning tool 176. The end tab 790 may situated adjacent to the base platform 134 which may operate as a détente for attachment of the oral cleaning tool 104. In accordance with embodiments of the present system, a larger saddle cross-sectional footprint his may enhance power transfer from the output shaft 120 to the oral cleaning tool 104. Additionally, by increasing the size of the saddle cross-sectional footprint, a larger socket 170 may be used which may aid insertion of the output shaft 120 into the socket 170. This may enhance user convenience.

Figure 7B:
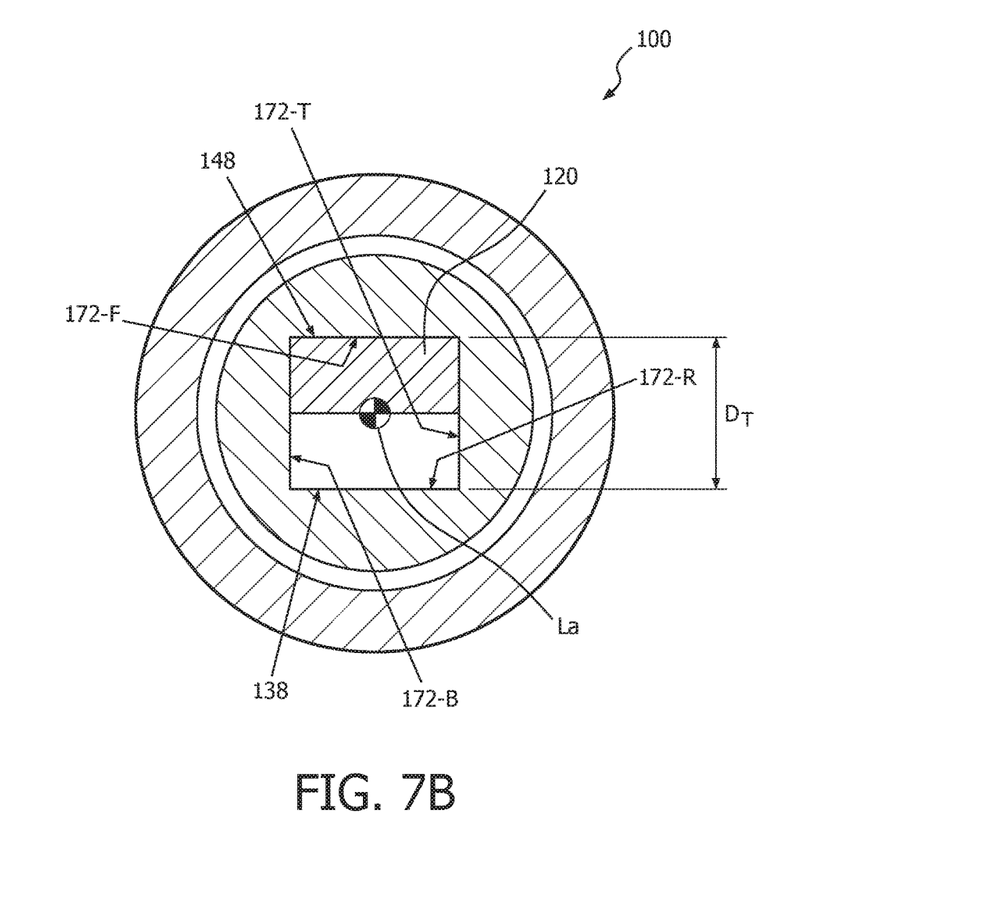
FIG. 7B shows a cross-sectional view of a portion of a tool and output shaft for example taken along lines 7B-7B such as may be of FIG. 7A in accordance with embodiments of the present system.

FIG. 7B shows a cross-sectional view of a portion of an automatic toothbrush 100 with an output shaft 120 for example taken along lines 7B-7B of FIG. 7A in accordance with embodiments of the present system. The top wall 172-T is opposed to a bottom wall 172-B of socket 170. By offsetting the saddles (138 and 148, shown) relative to the longitudinal axis (La) (which is assumed to correspond with a centerline of the output shaft 120 for the sake of clarity) a larger saddle cross-sectional footprint may be established. For example, assuming the saddle cross-sectional footprint may be defined as a distance between surfaces of opposed saddles (e.g., 148 and 138 which lie on opposite sides of the longitudinal axis (La) and may be represented by distance $D_T$. Accordingly, increasing the distance between (e.g., offset) the opposed saddles, increases $D_T$ and, thus, the saddle cross-sectional area. By increasing the distance $D_T$, a gripping area of the socket 170 may be increase in size which may provide for better coupling between the output shaft 120 and the oral cleaning tool 104 which may result in reduced acoustic emissions during use. Additionally, by offsetting the saddles, a thinner output shaft 120 may be used. Further, by using a thinner output shaft 120, a weight of the output shaft 120 may be balanced with an ultrasound actuator.

Figure 8:
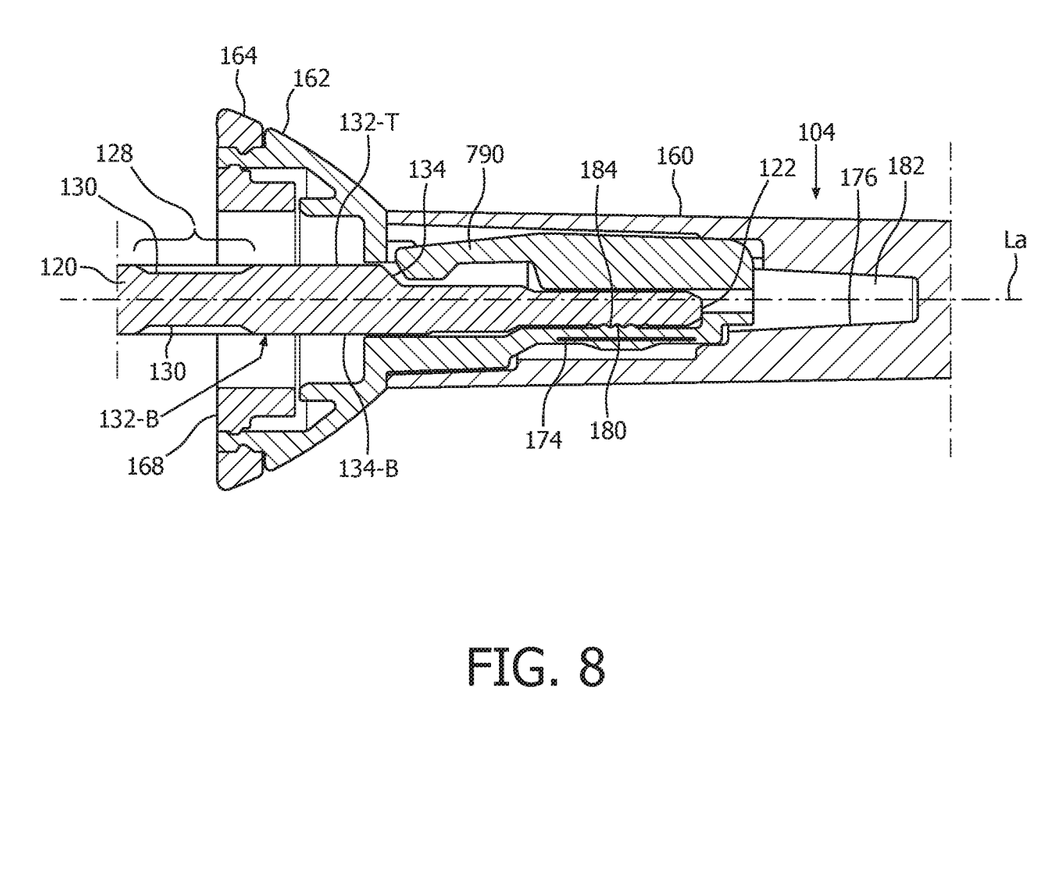
FIG. 8 shows a front planar side view of a portion of an output shaft and tool of an automatic toothbrush in accordance with embodiments of the present system.

FIG. 8 shows a front planar side view of a portion of an output shaft 120 and an oral cleaning tool 104 of the automatic toothbrush 100 in accordance with embodiments of the present system. The oral cleaning tool base 162 may include tab 180 which may engage a notched portion 184 of the output shaft 120 so as to releasably couple the tool 104 to the output shaft 120 during use. A biasing member 174 (e.g. steel c-clip spring) may be provided to bias the tab 180 against the notched portion 184. The end tab 790 may situated adjacent to the base platform 134 which may operate as a détente for attachment of the oral cleaning tool 104.

Figure 9:
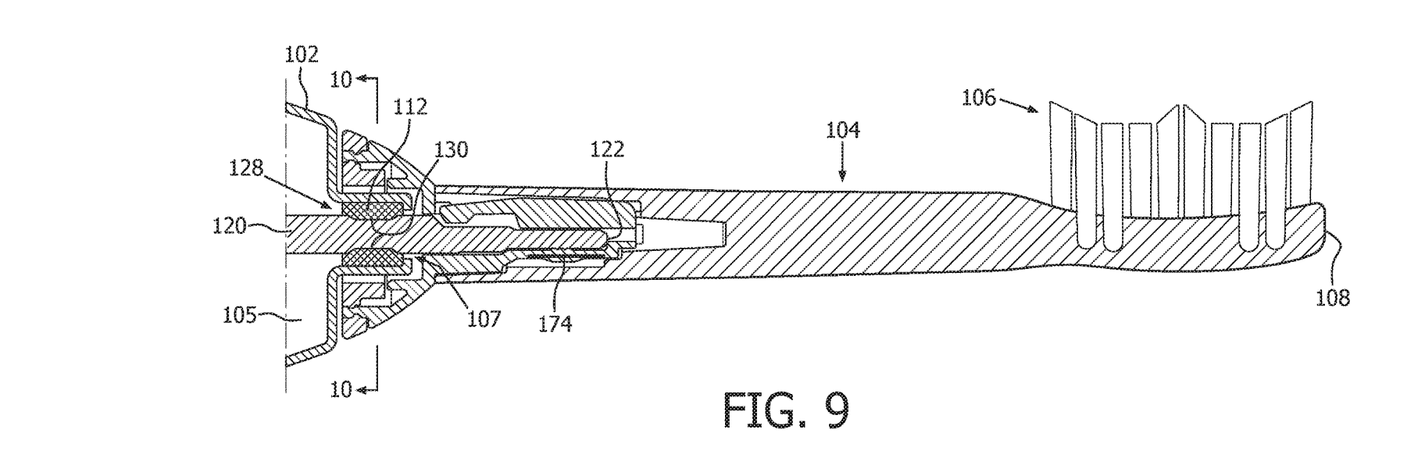
FIG. 9 shows a front planar side view of a portion of a body, output shaft, and tool of an automatic toothbrush in accordance with embodiments of the present system.

FIG. 9 shows a cross sectional view of a portion of a body 102, an output shaft 120, and an oral cleaning tool 104 of an automatic toothbrush 100 for example as for example taken along lines 9-9 of FIG. 1 in accordance with embodiments of the present system. The bristles 106 are situated at the distal end 108 of the oral cleaning tool 104. The body 102 may include an opening 107 through which a portion of the output shaft 120 may extend from a cavity 105 of the body 102. A seal 112 may be situated between the opening 107 and the sealing area 128 (e.g., a detent region) so as to seal the cavity 105 against penetration by liquids such as water. The seal 112 (e.g., a cavity seal) may be formed from any suitable material such as from a polymer seal material. The oral cleaning tool 104 is press fit upon the output shaft 120. As shown, the seal 112 may be coupled to an output shaft 120 at a sealing area 128 so as to seal the cavity 105 of the body 102 from liquids (e.g., water, etc.).

Figure 10:
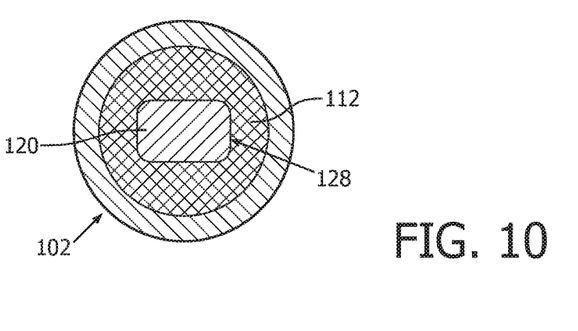
FIG. 10 shows a cross-sectional view of a portion of a body as may be for example taken along lines 10-10 of FIG. 9 in accordance with embodiments of the present system.

FIG. 10 shows a cross-sectional view of a portion of a body 102 for example taken along lines 10-10 of FIG. 9 in accordance with embodiments of the present system.

Figure 11:
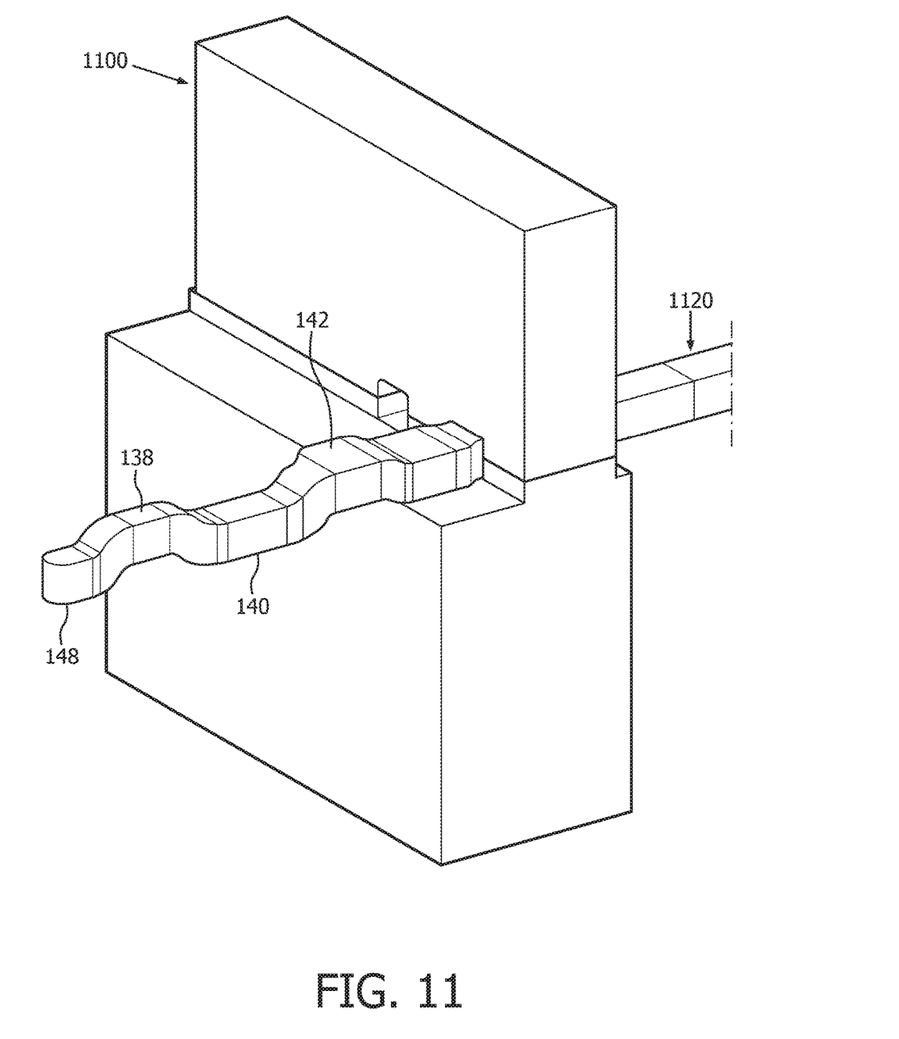
FIG. 11 is a perspective view of a portion of a tool stamp used to shape an output shaft blank in accordance with embodiments of the present system.

FIG. 11 is a perspective view of a portion of a tool stamp 1100 used to shape an output shaft blank 1120 in accordance with embodiments of the present system. The output shaft blank 1120 may be formed from a metal stamping and may have a generally flat shape. Then, during at least one stamping process such as a coining process (as shown), at least one area of the output shaft blank 1120 may be offset (e.g., at one or more folds, bends, etc.) so that the output shaft blank 1120 deviates from the generally flat shape away from or towards a longitudinal axis of the output shaft blank. In accordance with embodiments of the present system, the deviations may form for example, saddles 148, 138, 140, and 142, with the folds 145, 143, 141, 139, for example leading to the platform areas, the sealing area (e.g., see, FIGS. 2 and 4, the sealing area 128 and rounded edges 130), a notched portion (e.g., see, FIG. 8, the notched portion 184), etc. In this way, an output shaft 120 may be formed from the output shaft blank 1120 using for example a coining process that deforms the output shaft blank 1120 by a pressing operation of a tool stamp such as the tool stamp 1100. The tool stamp may include one or more stamping areas and/or two or more tool stamps may be utilized that include one or more stamping areas that complement (e.g., are a mirror image) a desired shape of the formed output shaft. Two or more tool stamps may be utilized together to stamp a given longitudinal portion of the output shaft blank.

In accordance with embodiments of the present system a unitary output shaft may be formed from a single piece of material using a simplified stamping process. Further, the unitary output shaft may reduce acoustic emissions compared to conventional drive methods.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. Further variations of the present system would readily occur to a person of ordinary skill in the art and are encompassed by the following claims. Accordingly, the specification and drawings are to be regarded in an illustrative manner and are not intended to limit the scope of the appended claims.

In interpreting the appended claims, it should be understood that: the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same item or hardware or software implemented structure or function; any of the disclosed elements may be comprised of hardware portions (e.g., including discrete and integrated electronic circuitry), software portions (e.g., computer programming), and any combination thereof; hardware portions may be comprised of one or both of analog and digital portions; any of the disclosed devices or portions thereof may be combined together or separated into further portions unless specifically stated otherwise; no specific sequence of acts or steps is intended to be required unless specifically indicated; the term "plurality of" an element includes two or more of the claimed element, and does not imply any particular range of number of elements; that is, a plurality of elements may be as few as two elements, and may include an immeasurable number of elements; and the term and/or and formatives thereof should be understood to mean that only one or more of the listed elements may need to be suitably present in the system in accordance with the claims recitation and in accordance with one or more embodiments of the present system.

The invention claimed is:

1. An automatic toothbrush, comprising:
   a body having opposed ends, a cavity situated between the opposed ends, and an opening situated at one of the opposed ends;
   an output shaft having first and second ends and extending through the opening such that the second end is outside of the cavity, the output shaft having at least two pairs of bends situated between the second end and the opening, each pair of bends comprising bends in opposite directions with at least one saddle situated there between; and
   an oral cleaning tool configured to be press fit onto that portion of the shaft which has the at least two pairs of bends to couple the cleaning tool to the body.

2. The automatic toothbrush of claim 1, wherein the output shaft is a unitary output shaft formed from a single sheet of material.

3. The automatic toothbrush of claim 1, wherein the oral cleaning tool comprises a socket configured to be press fit to the output shaft, the socket having a square or rectangular cross-section.

4. The automatic toothbrush of claim 1, wherein the oral cleaning tool has bristles on a distal end.

5. The automatic toothbrush of claim 1, wherein the plurality of bends define a plurality of saddles situated between the second end and the opening.

6. The automatic toothbrush of claim 5, wherein the output shaft is a unitary output shaft formed from a single piece of material having opposed first and second major surfaces.

7. An automatic toothbrush, comprising:
   a body defining a cavity and an opening leading to the cavity;
   an output shaft defining a longitudinal axis (La) and having opposed first and second ends, the output shaft extending through the opening such that the first end is located within the cavity and the second end is located outside of the cavity, the output shaft having a plurality of bends in opposite directions from each other wherein the output shaft deviates orthogonally to the longitudinal axis at the bends to define at least one saddle between two adjacent bends located between the opening and the second end;
   the automatic toothbrush further comprising an actuator situated within the cavity and configured to reciprocally drive the output shaft; and
   an oral cleaning tool having a handle and a socket disposed at one end of the handle, the oral cleaning tool configured to be press fit onto the second end of the output shaft.

8. The automatic toothbrush of claim 7, wherein a cross-sectional shape of the output shaft varies between the opening and the second end of the output shaft.

9. The automatic toothbrush of claim 7, wherein the output shaft further comprises a detent portion situated at the opening and having a plurality of rounded edges configured to receive a shaft seal for sealing the cavity.

10. The automatic toothbrush of claim 7, wherein the output shaft is a unitary output shaft formed from a single sheet of material.

* * * * *